US011821836B2

United States Patent
Deliwala

(10) Patent No.: US 11,821,836 B2
(45) Date of Patent: Nov. 21, 2023

(54) FULLY COMPENSATED OPTICAL GAS SENSING SYSTEM AND APPARATUS

(71) Applicant: Analog Devices, Inc., Wilmington, MA (US)

(72) Inventor: Shrenik Deliwala, Andover, MA (US)

(73) Assignee: ANALOG DEVICES, INC., Wilmington, MA (US)

(*) Notice: Subject to any disclaimer, the term of this patent is extended or adjusted under 35 U.S.C. 154(b) by 43 days.

(21) Appl. No.: 17/327,172

(22) Filed: May 21, 2021

(65) Prior Publication Data

US 2022/0011223 A1 Jan. 13, 2022

Related U.S. Application Data

(60) Provisional application No. 63/051,042, filed on Jul. 13, 2020.

(51) Int. Cl.
*G01N 21/3504* (2014.01)
*G01N 21/01* (2006.01)

(52) U.S. Cl.
CPC ......... *G01N 21/3504* (2013.01); *G01N 21/01* (2013.01); *G01N 2021/3513* (2013.01); *G01N 2201/0636* (2013.01); *G01N 2201/1211* (2013.01)

(58) Field of Classification Search
CPC .............. G01N 21/3504; G01N 21/01; G01N 2021/3513; G01N 2201/0636; G01N 2201/1211
See application file for complete search history.

(56) References Cited

U.S. PATENT DOCUMENTS

| | | |
|---|---|---|
| 4,148,022 A | 4/1979 | Hetznecker |
| 4,181,439 A | 1/1980 | Horvath et al. |
| RE32,105 E | 4/1986 | Enemark |
| 4,618,771 A | 10/1986 | Farren |
| 4,830,496 A | 5/1989 | Young |
| 5,129,401 A | 7/1992 | Corenman et al. |
| 5,382,341 A | 1/1995 | Aroutiounian et al. |

(Continued)

FOREIGN PATENT DOCUMENTS

| | | |
|---|---|---|
| CA | 2386899 A1 | 4/2001 |
| CN | 104246617 B | 9/2018 |

(Continued)

OTHER PUBLICATIONS

Paul et al., *Investigation of Gas Sensor Based on Differential Optical Absorption Spectroscopy Using Photonic Crystal Fiber*, Alexandria Engineering Journal (2020), 59, 8 pages.

(Continued)

*Primary Examiner* — Jamil Ahmed
(74) *Attorney, Agent, or Firm* — ArentFox Schiff LLP

(57) ABSTRACT

System and apparatus for robust, portable gas detection. Specifically, this disclosure describes apparatuses and systems for optical gas detection in a compact package using two optical pathways. There is a need for a very compact, low-power, gas detection system for gases such as $CO_2$, NOx, water vapor, methane, etc. This disclosure provides an ultra-compact and highly stable and efficient optical measurement system based on principals of optical absorption spectroscopy using substantially collinear pathways.

20 Claims, 4 Drawing Sheets

(56) References Cited

U.S. PATENT DOCUMENTS

| | | | |
|---|---|---|---|
| 5,420,440 A | 5/1995 | Ketler et al. | |
| 5,444,249 A | 8/1995 | Wong | |
| 5,568,129 A | 10/1996 | Sisselman et al. | |
| 5,689,114 A | 11/1997 | Miyazaki et al. | |
| 5,781,291 A | 7/1998 | So et al. | |
| 5,957,858 A | 9/1999 | Micheels et al. | |
| 5,966,077 A | 10/1999 | Wong et al. | |
| 5,973,326 A | 10/1999 | Parry et al. | |
| 6,194,735 B1 | 2/2001 | Martin | |
| 6,599,253 B1* | 7/2003 | Baum | G01N 33/497 356/303 |
| 8,003,945 B1 | 8/2011 | Wong | |
| 8,232,885 B2 | 7/2012 | Hoshino et al. | |
| 11,073,467 B2 | 7/2021 | Santangelo et al. | |
| 11,079,321 B2 | 8/2021 | Castagna et al. | |
| 2003/0011769 A1 | 1/2003 | Rakuljic et al. | |
| 2004/0072535 A1 | 4/2004 | Schneider et al. | |
| 2005/0077489 A1 | 4/2005 | Knapp et al. | |
| 2007/0013883 A1 | 1/2007 | Park | |
| 2007/0145275 A1 | 6/2007 | Wong | |
| 2007/0221848 A1 | 9/2007 | Johnson et al. | |
| 2008/0316489 A1 | 12/2008 | Ludwig et al. | |
| 2009/0213380 A1 | 8/2009 | Appel et al. | |
| 2009/0235720 A1 | 9/2009 | Smith | |
| 2009/0257064 A1 | 10/2009 | Tkachuk | |
| 2009/0268204 A1 | 10/2009 | Tkachuk | |
| 2011/0042570 A1 | 2/2011 | Wong | |
| 2011/0178420 A1 | 7/2011 | Ridder et al. | |
| 2012/0135405 A1 | 5/2012 | Toumbas et al. | |
| 2012/0140231 A1 | 6/2012 | Knox et al. | |
| 2012/0267532 A1 | 10/2012 | Udrea et al. | |
| 2013/0066173 A1* | 3/2013 | Addison | A61B 5/029 600/323 |
| 2013/0075615 A1 | 3/2013 | Starta et al. | |
| 2013/0286393 A1 | 10/2013 | Erdtmann | |
| 2014/0070101 A1 | 3/2014 | Matsushima et al. | |
| 2015/0129767 A1 | 5/2015 | Kouznetsov et al. | |
| 2015/0219491 A1 | 8/2015 | Lee et al. | |
| 2016/0005921 A1 | 1/2016 | Suchalkin et al. | |
| 2016/0042638 A1 | 2/2016 | Sangha et al. | |
| 2016/0231239 A1 | 8/2016 | Kotidis et al. | |
| 2017/0191930 A1 | 7/2017 | Warren et al. | |
| 2017/0241904 A1 | 8/2017 | Barritault et al. | |
| 2018/0348121 A1 | 12/2018 | Deliwala | |
| 2019/0094134 A1 | 3/2019 | Solovyov et al. | |
| 2020/0209158 A1 | 7/2020 | Nikolaenko et al. | |
| 2021/0072082 A1 | 3/2021 | Valouch et al. | |
| 2021/0132019 A1 | 5/2021 | Heffels et al. | |

FOREIGN PATENT DOCUMENTS

| | | |
|---|---|---|
| DE | 10 2017 23196 A1 | 1/2019 |
| EP | 896216 A2 | 2/1999 |
| JP | H09229585 A | 9/1997 |
| WO | 9914576 A2 | 3/1999 |
| WO | 2007080398 A1 | 7/2007 |
| WO | 2009150325 A1 | 12/2009 |

OTHER PUBLICATIONS

Yang et al., *Simultaneous Measurement of Gas Absorption and Path Length by Employing the First Harmonic Phase Angle in Wavelength Modulation Spectroscopy*, Optics Express, vol. 28, No. 3, Feb. 3, 2020, 9 pages.

Extended European Search Report in EP20179106.8, dated Jan. 18, 2021, 16 pages.

International Search Report and Written Opinion in PCT/US2018/035203, dated Aug. 29, 2018, 11 pages.

International Search Report and Written Opinion in PCT/US2021/041378, dated Jan. 28, 2022, 18 pages.

Invitation to Pay Additional Fees in PCT/US2021/041378, dated Oct. 19, 2021, 10 pages.

\* cited by examiner

FULLY COMPENSATED OPTICAL GAS SENSING SYSTEM AND APPARATUS

CROSS-REFERENCE TO RELATED APPLICATIONS

This application is related to and claims the benefit of priority under 35 U.S.C. § 119(e) to U.S. Provisional Patent Application No. 63/051,042 entitled, "FULLY COMPENSATED OPTICAL GAS SENSING SYSTEM" filed on Jul. 13, 2020 and related to U.S. patent application Ser. No. 15/993,188 now U.S. Pat. No. 10,866,185 entitled, "COMPACT OPTICAL GAS DETECTION SYSTEM AND APPARATUS" filed on May 30, 2018, U.S. patent application Ser. No. 16/872,758 entitled, "GAS DETECTION USING DIFFERENTIAL PATH LENGTH MEASUREMENT" filed on May 12, 2020, all of which are hereby incorporated by reference in their entirety.

FIELD OF THE DISCLOSURE

The present disclosure relates to portable gas detection. More specifically, this disclosure describes apparatuses and systems for optical gas detection using differential path lengths.

BACKGROUND

A nondispersive infrared sensor (or NDIR sensor) is a simple spectroscopic sensor often used as a gas detector. It is nondispersive in the sense of optical dispersion since the infrared energy is allowed to pass through the atmospheric sampling chamber without deformation.

It is also non-dispersive in the fact that no dispersive element (e.g., a prism or diffraction grating as is often present in other spectrometers) is used to separate out (like a monochromator) the broadband light into a narrow spectrum suitable for gas sensing. The majority of NDIR sensors use a broadband lamp source and an optical filter to select a narrow band spectral region that overlaps with the absorption region of the gas of interest. In this context narrow may be 50-300 nm bandwidth. Modern NDIR sensors may use Microelectromechanical systems (MEMs) or mid IR LED sources, with or without an optical filter.

The main components of an NDIR sensor are an infrared source (lamp), a sample chamber or light tube, a light filter and an infrared detector. The IR light is directed through the sample chamber towards the detector. In parallel there is another chamber with an enclosed reference gas, typically nitrogen. The gas in the sample chamber causes absorption of specific wavelengths according to the Beer-Lambert law, and the attenuation of these wavelengths is measured by the detector to determine the gas concentration. The detector has an optical filter in front of it that eliminates all light except the wavelength that the selected gas molecules can absorb.

Ideally other gas molecules do not absorb light at this wavelength, and do not affect the amount of light reaching the detector however some cross-sensitivity is inevitable. For instance, many measurements in the IR area are cross sensitive to H2O so gases like CO2, SO2 and NO2 often initiate cross sensitivity in low concentrations.

A common application is to use a NDIR (non-dispersive infrared absorbance) sensor to monitor CO2. Most molecules can absorb infrared light, causing them to bend, stretch or twist. The amount of IR light absorbed is proportional to the concentration. The energy of the photons is not enough to cause ionization, and thus the detection principle is very different from that of a photoionization detector (PID). Ultimately, the energy is converted to kinetic energy, causing the molecules to speed up and thus heat the gas. A familiar IR light source is an incandescent household bulb. Each molecule absorbs infrared light at wavelengths representative of the types of bonds present.

Many techniques have been proposed which typically consist of a broadband light source. Unfortunately, they require relatively long optical paths which reduce light collection efficiencies. The inventor of the present disclosure has identified these shortcomings and recognized a need for a more elegant, robust, compact optical gas detection measurement system with high collection efficiency. That is, the inventor has come up with a compact, low-power, optical gas detection apparatus which can be mass produced via packaging without yielding accuracy.

Additionally, the current state of the art uses color wheels or filters disposed at the photodetectors. Specifically, one color (at wavelength, $\lambda_1$) is measured for an absorption for a particular gas. The reference measure is typically taken at another color (at wavelength, $\lambda_2$) via color wheel or second sensor with a filter centered at, $\lambda_2$. Gas concentration per unit volume is based upon absorption spectroscopy. However, these techniques fail to account for the variation of several parameters, in particular, thermal drift, filter bandwidth and sensitivity, variance of the source as a function of wavelength, etc.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

System and apparatus for robust, portable gas detection. Specifically, this disclosure describes apparatuses and systems for optical gas detection in a compact package using two optical pathways. There is a need for a very compact, low-power, gas detection system for gases such as CO2, NOx, water vapor, methane, etc. This disclosure provides an ultra-compact and highly stable and efficient optical measurement system based on principals of optical absorption spectroscopy using substantially collinear pathways.

It not only reduces the size of the instrument as well its power consumption by more than an order of magnitude making it possible to deploy it widely, but increases accuracy. This is accomplished by measuring two optical path lengths subject to the same conditions and thereby concluding a result, ceteris paribus. There has been an identified need for large number of distributed gas sensors to improve human health, environment, and save energy usage.

According to one aspect of the present disclosure, gas absorption measurement device, measurement of the differential path length ratio at two wavelengths—the first wavelength is disposed at the wavelength of absorption of the target gas and the second wavelength is disposed such that it us not absorbed at any of the gases present in the measurement gas mixture.

According to another aspect of the present disclosure, gas absorption measurement device, both wavelengths follow substantially identical optical path through the gas sampling optics starting with the optical filter.

According to another aspect of the present disclosure, gas absorption measurement device is derived from formation of RoR as described from the novel differential path length (DPL) ratio.

According to another aspect of the present disclosure, gas absorption measurement device in which 2nd LED is placed in close proximity to the first LED and first LED acts like a secondary reflector to the second LED such that the optical path of the light rays from the second LED after scattering of the first LED is substantially identical.

According to another aspect of the present disclosure, gas absorption measurement device in which 1st/2nd LED is placed below or stacked on top of 2nd/1st LED.

According to another aspect of the present disclosure, gas absorption measurement device in which one physical LED produces two different wavelengths controllable by electric current.

According to another aspect of the present disclosure, gas absorption measurement device in which the first LED and filter together have absorption region beyond the target gas to include another gas while the second LED and the filter has absorption only at the other gas.

According to one aspect of the present disclosure, gas absorption measurement device (or working fluid absorption device) comprises a light source forming a common light path, one or more filters filtering the common light path, a collimator disposed in the common light path, a beam splitter to split the common light path and two or more detectors, each of which to collect the split light path.

According to another aspect of the present disclosure, gas absorption measurement device (or working fluid absorption device) is configure to dispose the two or detectors at two (or more accordingly) different distances from the light source with each detector measuring light transmission after two different gas absorption path lengths.

According to another aspect of the present disclosure, gas absorption measurement device (or working fluid absorption device) further comprises collector optic before the detectors.

According to another aspect of the present disclosure, gas absorption measurement device (or working fluid absorption device), the beam splitter can be a polarizing beam splitter (PBS), a half-wave plate, a half-silvered mirror, a Fresnel prism, or any other suitable optic.

According to another aspect of the present disclosure, gas absorption measurement device (or working fluid absorption device) further comprises one or more waveguides.

According to another aspect of the present disclosure, the waveguides provide for openings for the diffusion of gas molecules.

According to another aspect of the present disclosure, the optical filter can include an absorptive filter and/or interference or dichroic filter.

According to another aspect of the present disclosure, the light source can include a light emitting device (LED) or other suitable device.

According to another aspect of the present disclosure, the collection optics can include a convex or concave lens.

According to another aspect of the present disclosure, the detectors are photosensitive elements and can be one or more of the following: photodetectors, photodiodes (PDs), avalanche photodiodes (APDs), single-photon avalanche photodiode (SPADs), photomultipliers (PMTs).

According to another aspect of the present disclosure, the differences in the path length is employed after filtering of the light source for a specific gas absorption.

According to another aspect of the gas absorption measurement device (or working fluid absorption device), a ratio of the two detector signals is used to measure the concentration of the working fluid.

According to another aspect of the gas absorption measurement device (or working fluid absorption device), the ratio of the two detectors is saved during calibration step with known condition and subsequently used for future calculations.

According to another aspect of the gas absorption measurement device (or working fluid absorption device), concentration of a predetermined gas is calculated.

According to another aspect of the present disclosure, the predetermined gas may be CO2, water vapor, methane CH4, NO, as well as vapors of various alcohols.

According to another aspect of the present disclosure, the predetermined gas may be any of the gases used in anesthesia.

According to another aspect of the present disclosure, the predetermined gas may be vapors of diesel, kerosene, or gasoline.

According to another aspect of the present disclosure, multiple gases may be simultaneously detected by using multiple detectors with optical filters chosen for each of the gases and using a broadband light source.

According to another aspect of the present disclosure, the predetermined gases may be CO2 and alcohol vapor which are simultaneously detected for breadth analysis.

According to another aspect of the present disclosure, the predetermined gases may be water and alcohol vapor which are simultaneously detected for breadth analysis.

According to another aspect of the disclosure, the gas absorption measurement device (or working fluid absorption device) is disposed on a substrate.

According to another aspect of the present disclosure, the gas absorption measurement device (or working fluid absorption device) further comprises an optical cap to which is affixed to the substrate.

According to another aspect of the present disclosure, the inner shape of the cap forms a mirror in which the mirror shape is derived from the two elliptical mirror surfaces inclined substantially at 45 degrees to provide high collection of the light source to the detector.

According to another aspect of the present disclosure, the cap provides for openings for the diffusion of gas molecules.

According to another aspect of the present disclosure, the substrate and the cap provide a method of alignment to each other.

According to another aspect of the present disclosure, the opto-electronic package for measurement of absorption of light further comprises a substrate with at least two detectors disposed thereon.

According to another aspect of the present disclosure, wherein the first detector acts as a reference detector that is measures light such that its signal is substantially insensitive to the absorption by a predetermined gas.

According to another aspect of the present disclosure, the second detector that may have either optical filter attached to it or provided on top of it to make it substantially sensitive to the absorption by the predetermined gas.

According to another aspect of the present disclosure, the opto-electronic package for measurement of absorption of light further comprises many detectors in which at least one detector acts as a reference detector and the other detectors optical filters have applied to them so as to detect different gases present in the cavity.

According to another aspect of the present disclosure, the light source may be a thermal light source.

According to another aspect of the present disclosure, the opto-electronic package for measurement of absorption of light further comprises a substrate with a light source disposed on it. LED may have a center wavelength from 0.2-12 μm.

According to another aspect of the present disclosure, the detector may use direct photon absorption or may use indirect method of measurement that includes conversion to heat to measure light flux.

According to another aspect of the present disclosure, direct photon detectors include detectors made from PbSe, PbS, HgCdTe, GaSb/InAs superlattice etc.

According to another aspect of the present disclosure, indirect thermal detectors include pyroelectrics, bolometers, etc.

According to another aspect of the present disclosure, the opto-electronic package for measurement of absorption of light further comprises that the openings to the cavity that forms the cap may be covered with fine mesh to prevent larger dust particles from entering the cavity.

According to another aspect of the present disclosure, the opto-electronic package for measurement of absorption of light further comprises that the package is constructed with "base package" that can be tested separately from the gas chamber and the two combined by assembly to form the complete gas detection system.

The drawings show exemplary gas detections circuits and configurations. Variations of these circuits, for example, changing the positions of, adding, or removing certain elements from the circuits are not beyond the scope of the present invention. The illustrated smoke detectors, configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

Figure 1:
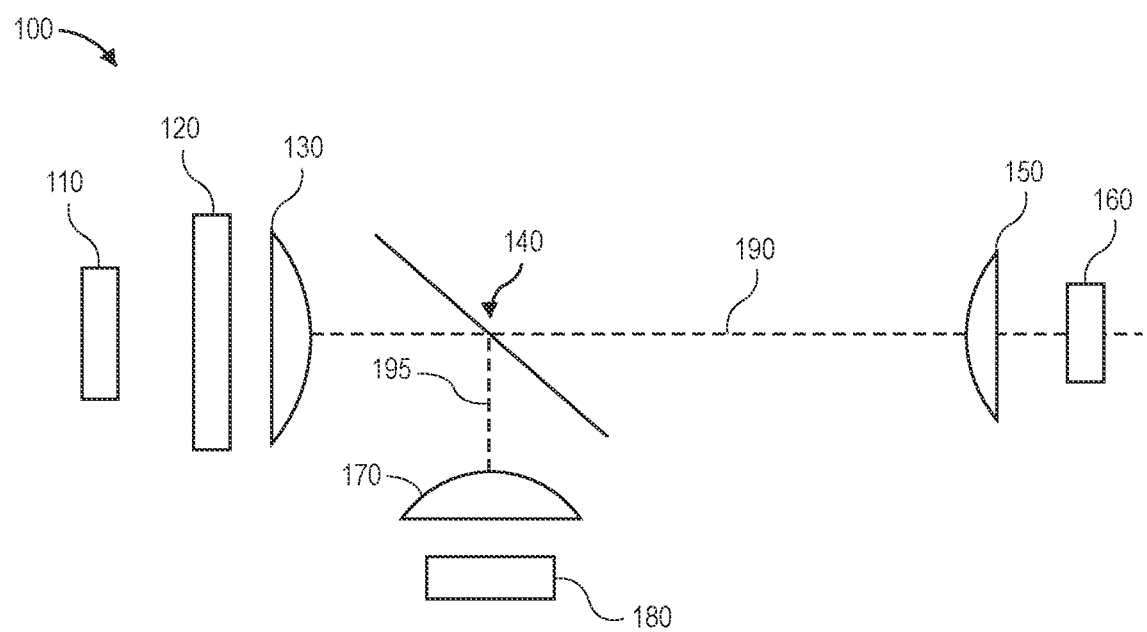
FIG. 1 depicts an exemplary differential path length measurement system for measuring gas concentration using absorption spectroscopy, in accordance with some embodiments of the disclosure provided herein.

The present disclosure relates to portable gas detection. More specifically, this disclosure describes apparatuses and systems for optical gas detection using differential path. The inventor of the present disclosure contemplates filtering a common beam path, splitting it to measure light absorption at two different light length paths and then calculating the concentration of a predetermined gas.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

One of the most popular technique for quantitative measurement of the industrially significant gases such as $CO_2$, $NO_x$, water vapor, methane etc. is carried out by optical absorption. Most of these gases have strong vibrational absorption spectra in the 1-12 μm region of electromagnetic spectrum and include various vibrational modes and its overtones.

A fundamental measurement technique consists of a measuring changes in the extinction of the light source at a particular wavelength of interest as the concentration of the target gas is varied. This technique is popularly called non-dispersive infra-red (NDIR) technique.

Many devices are available on the market. They typically consist of a broadband light source—thermal such as light bulb or a compact heater or an LED—whose output is passed thru an optical system that provides a relatively long path length for absorption of gas and a detector system to measure extinction. Small holes in the optical system allows the gas to diffuse into the light path.

The detector system itself may consist of two detectors. One detector provides a reference signal and is specifically tuned to reduce or avoid gas absorption lines of interest to measure drift and changes in the light source and condition of the optical channel. The other detector is tuned to the wavelength of absorption of the gas to be measured.

Many configurations of the optical systems have been proposed in the past, and some of these devices are available on the market. One of the most popular gases to be measured is $CO_2$. In the discussion below on the design of a novel optical package, the focus will be on $CO_2$ gas to make the discussion specific, but the principal applies to many of the industrially relevant gases mentioned earlier and is quite general.

Furthermore, the present disclosure will focus on systems that use room temperature detectors and are not cooled since cooling adds cost, increases power consumption, and increases system complexity. However, active and/or passive cooling are not beyond the scope of the present invention.

A better method for measuring absolute gas concentration is disclosed. The method applies equally well to absorbance measurement in liquids. This method applies to any fluid (gas or liquid) that can be placed in the path between light source and two detectors.

A large body of literature exists that use reference detector to measure concentration of gas. The largest market is non-dispersive IR measurements (NDIR) in which an optical filter is used to isolate the absorbance of the gas of interest.

Some use a single detector and source and pre-calibrated look-up tables to compensate for temperature, humidity, aging etc. while more precise systems use two different detectors with different filter characteristics or vary the filter in time with the same detector. The state of the art looks similar to that in FIG. 1.

FIG. 1 illustrates an exemplary optical gas detection measurement system utilizing filters disposed proximally to the detectors, in accordance with some embodiments of the disclosure provided herein. In some embodiments, light source is powered to shine down a sampling tube. The light source is usually broadband, but the present embodiment uses an infrared (IR) source which is suitable for detecting $CO_2$ gas.

Gas containing $CO_2$ is passed through the sampling tube through vents or ports. Some light absorption occurs as a function of the concentration and chemical composition of the target gas. Meaning, different gasses absorb light at different wavelengths (bandwidths, really). Accordingly, higher concentrations of targeted gasses with absorb more light at that associated wavelength. The goal of any NDIR system is to accurately determine how much light is absorbed/scattered in order to extrapolate the density of gas (i.e., partial pressure of the gas).

The gas in the sample chamber causes absorption of specific wavelengths according to the Beer-Lambert law, and the attenuation of these wavelengths is measured by the detector to determine the gas concentration. Carbon dioxide has a characteristic absorbance band in the infrared (IR) region at a wavelength of 4.26 µm. This means that when IR radiation is passed through a gas containing CO2, part of the radiation is absorbed. Therefore, the amount of radiation passing through the gas depends on the amount of CO2 present, and this can be detected with an IR detector.

This is accomplished by using two optical bandpass filters and two thermopiles. A thermopile is an electronic device that converts thermal energy into electrical energy. It is composed of several thermocouples connected usually in series or, less commonly, in parallel. Such a device works on the principle of the thermoelectric effect, i.e., generating a voltage when its dissimilar metals (thermocouples) are exposed to a temperature difference.

One bandpass filter is used as a reference band and typically doesn't significantly overlap with the absorption signal band. As previously described, the absorption signal band corresponds to the target gas. The two are compared (e.g., ratio, etc.) and a determination can be made about the concentration of the target gas.

A system such as this does need to be calibrated. Specifically, some measurement baseline needs to be taken before target gas detection. Nevertheless, the present system is susceptible to wavelength drift from the light source, which represents one of the shortcomings of the present state of the art.

While versatile in that the present embodiment may detect numerous gasses at once, the present system suffers from the previous embodiment. That is, the system requires calibration and is susceptible from wavelength and intensity drift, particularly because it does not have a reference channel measurement.

The idea in the state-of-the-art systems is that the ratio of the reference channel to the filtered channel—corresponding to the specific gas—removes the intensity variation in the source over time as well as common changes in the performance of the detectors. In these methods of measuring gas concentration, shifts in the wavelength spectrum of the light as well as subtle changes in the optical filters cannot be removed directly from the measurement. While alleviating some of the issues of drift, it still requires complex calibration.

Some state-of-the-art systems (e.g., Vaisala) use a Fabry-Perot (FP) cavity-based system use the same detector which receives radiation from a single light source as the filter is tuned alternately between "on gas absorbance" and "off gas absorbance" to measure the gas absorbance. However, this does not properly compensate for the spectral shifts in the light source or the filter. In most of cases of IR measurement of gases, "off-absorption filter" has to be many 100's of nm from the "on-absorption filter" due to the width of the absorption features. This is sufficiently separated in wavelength, that the ratio cannot fully compensate for the spectral shape changes in LED and other light sources over time and temperature.

In all previous designs that the inventor has reviewed, the reference channel uses a different filter than the measurement channel to track the light source's intensity variation. In Vaisala's sensor, FP cavity is used and filter is tuned to be on and off the gas absorption wavelengths alternatively in time.

One of ordinary skill can appreciate the following novel features of the disclosure. Other benefits are not beyond the scope of the present disclosure. The present disclosure is highly independent of the LED and filter performance over temperature, intensity, etc. as well as any changes in the wavelength spectrum of the light source and filters and other optical elements.

Additionally, all spectral changes over are naturally removed from the measurement. This includes changes in intensity either due to electrical or optical system drifts.

The present disclosure provides the benefits of ratio metric measurement cancelling most of the drifts even amongst the two detectors to the extent that the two detectors are identically manufactured.

The present disclosure also provides for highly simplified calibration with a single measurement at a known concentration of the species of interest.

Last, the present disclosure is easy to implement as current solutions are more tractable. As such, calibration procedure is highly simplified during manufacturing.

FIG. 1 depicts an exemplary differential path length measurement system 100 for measuring gas concentration using absorption spectroscopy, in accordance with some embodiments of the disclosure provided herein. Differential path length measurement system 100 comprises light source 110, filter 120, collimating lens 130, beamsplitter 140, reference collection lens 170, reference detector 180, signal collection lens 110, and signal detector 160.

In one or more embodiments, light source 110 is a light emitting diode (LED), such as, an infrared (IR) light emitting diode. However, other embodiments can have light emitting diodes having shorter wavelengths, such as that in the visible or ultraviolet regime. In yet other embodiments, a plurality of multiple wavelengths can be used. Any suitable, compact light producing device is not beyond the scope of the present disclosure-whether, broadband lamps, coherent, incandescent, incoherent bulb, lasers, or even thermal black-body radiation, etc.

In one or more embodiments filter 120 is a dichroic filter, at least in part. A dichroic filter, thin-film filter, or interference filter is a very accurate color filter used to selectively pass light of a small range of colors while reflecting other colors. By comparison, dichroic mirrors and dichroic reflectors tend to be characterized by the color(s) of light that they reflect, rather than the color(s) they pass.

While dichroic filters are used in the present embodiment, other optical filters are not beyond the scope of the present invention, such as, interference, absorption, diffraction, grating, Fabry-Perot, etc. An interference filter consists of multiple thin layers of dielectric material having different refractive indices. There also may be metallic layers. In its broadest meaning, interference filters comprise also etalons that could be implemented as tunable interference filters. Interference filters are wavelength-selective by virtue of the interference effects that take place between the incident and reflected waves at the thin-film boundaries. In other embodiments, a color wheel with an optical chopper can be used as the filter 120.

Collimating lens 130 is a collimator. In optics, a collimator may consist of a curved mirror or lens with some type of light source and/or an image at its focus. This can be used to replicate a target focused at infinity with little or no parallax. The purpose of the collimating lens 130 is to direct the light rays in coaxial light path toward beamsplitter 140.

Beamsplitter 140 is a beamsplitter which is known in the art. A beam splitter (or beamsplitter) is an optical device that splits a beam of light in two. It is a crucial part of many optical experimental and measurement systems, such as interferometers, also finding widespread application in fiber optic telecommunications.

In its most common form, a cube, a beamsplitter 140 is made from two triangular glass prisms which are glued together at their base using polyester, epoxy, or urethane-based adhesives. The thickness of the resin layer is adjusted such that (for a certain wavelength) half of the light incident through one "port" (i.e., face of the cube) is reflected and the other half is transmitted due to frustrated total internal reflection. Polarizing beam splitters, such as the Wollaston prism, use birefringent materials to split light into two beams of orthogonal polarization states.

In other embodiments, beamsplitter 140 is a half-silvered mirror. This comprises an optical substrate, which is often a sheet of glass or plastic, with a partially transparent thin coating of metal. The thin coating can be aluminum deposited from aluminum vapor using a physical vapor deposition method. The thickness of the deposit is controlled so that part (typically half) of the light which is incident at a 45-degree angle and not absorbed by the coating or substrate material is transmitted, and the remainder is reflected.

A very thin half-silvered mirror used in photography is often called a pellicle mirror, which can also be used in some embodiments. To reduce loss of light due to absorption by the reflective coating, so-called "swiss cheese" beam splitter mirrors have been used. Originally, these were sheets of highly polished metal perforated with holes to obtain the desired ratio of reflection to transmission. Later, metal was sputtered onto glass so as to form a discontinuous coating, or small areas of a continuous coating were removed by chemical or mechanical action to produce a very literally "half-silvered" surface.

In yet another embodiment, instead of a metallic coating, a dichroic optical coating may be used. Depending on its characteristics, the ratio of reflection to transmission will vary as a function of the wavelength of the incident light. Dichroic mirrors are used in some ellipsoidal reflector spotlights to split off unwanted infrared (heat) radiation, and as output couplers in laser construction.

In still another embodiment, a third version of the beamsplitter 140 is a dichroic mirrored prism assembly which uses dichroic optical coatings to divide an incoming light beam into a number of spectrally distinct output beams. Such a device was used in three-pickup-tube color television cameras and the three-strip Technicolor movie camera. It is currently used in modern three-CCD cameras. An optically similar system is used in reverse as a beam-combiner in three-LCD projectors, in which light from three separate monochrome LCD displays is combined into a single full-color image for projection.

As enumerated, any beam splitter or optical circulator can be used. Optical circulators which have the property to conserve power but greatly increase the complexity and cost. However, any suitable optical device, e.g., polarizing beam splitter, half-wave plate, half silvered mirror, etc., is not beyond the scope of the present invention.

In practice, collimated light coming from collimating lens 130 get bifurcated into two beams, 195, 190. Beam 195 is used as the reference beam, which beam 190 is used as the signal beam. Their geometries are known, as well as their respective pathlengths. The significance of which will be described in greater detail later in the disclosure.

In one or more embodiments, reference collection lens 370 and signal collection lens 150 are optical lenses. An optical lens is a transmissive optical device that focuses or disperses a light beam by means of refraction. A simple lens consists of a single piece of transparent material, while a compound lens consists of several simple lenses (elements), usually arranged along a common axis. Lenses are made from materials such as glass or plastic, and are ground and polished or molded to a desired shape.

A lens can focus light to form an image, unlike a prism, which refracts light without focusing. Devices that similarly focus or disperse waves and radiation other than visible light are also called lenses, such as microwave lenses, electron lenses, acoustic lenses, or explosive lenses.

Most lenses are spherical lenses: their two surfaces are parts of the surfaces of spheres. Each surface can be convex (bulging outwards from the lens), concave (depressed into the lens), or planar (flat). The line joining the centers of the spheres making up the lens surfaces is called the axis of the lens.

Lenses are classified by the curvature of the two optical surfaces. A lens is biconvex (or double convex, or just convex) if both surfaces are convex. If both surfaces have the same radius of curvature, the lens is equiconvex. A lens with two concave surfaces is biconcave (or just concave). If one of the surfaces is flat, the lens is plano-convex or plano-concave depending on the curvature of the other surface. A lens with one convex and one concave side is convex-concave or meniscus. It is this type of lens that is most commonly used in corrective lenses.

If the lens is biconvex or plano-convex, a collimated beam of light passing through the lens converges to a spot (a focus) behind the lens. In this case, the lens is called a positive or converging lens. For a thin lens in air, the distance from the lens to the spot is the focal length of the lens, which is commonly represented by f in diagrams and equations. An extended hemispherical lens is a special type of piano-convex lens, in which the lens's curved surface is a full hemisphere and the lens is much thicker than the radius of curvature.

If the lens is biconcave or piano-concave, a collimated beam of light passing through the lens is diverged (spread); the lens is thus called a negative or diverging lens. The beam, after passing through the lens, appears to emanate from a particular point on the axis in front of the lens. For a thin lens in air, the distance from this point to the lens is the focal length, though it is negative with respect to the focal length of a converging lens.

Convex-concave (meniscus) lenses can be either positive or negative, depending on the relative curvatures of the two surfaces. A negative meniscus lens has a steeper concave surface and is thinner at the center than at the periphery. Conversely, a positive meniscus lens has a steeper convex surface and is thicker at the center than at the periphery. An ideal thin lens with two surfaces of equal curvature would have zero optical power, meaning that it would neither converge nor diverge light.

All real lenses have nonzero thickness, however, which makes a real lens with identical curved surfaces slightly positive. To obtain exactly zero optical power, a meniscus lens must have slightly unequal curvatures to account for the effect of the lens' thickness.

In practice, both collective lenses serve to focus light onto photodetectors 160, 180 are sensors of light or other electromagnetic energy. Photodetector 160, 180 have p-n junctions that converts light photons into current. The absorbed photons make electron-hole pairs in the depletion region, which is used to detect received light intensity. In some embodiments, photodetectors 160, 180 are photodiodes or phototransistors. However, any light detecting means, e.g., avalanche, photo-multiplier tube, etc. is not beyond the scope of the present disclosure.

Pursuant to FIG. 1, it can be demonstrated:

$$R = \frac{S_1}{S_2} = \frac{LS\ F\ D_1\ \exp(-\alpha_{gas}c_{gas}L_1)}{LS\ F\ D_2\ \exp(-\alpha_{gas}c_{gas}L_2)} = \frac{D_1}{D_2}\exp(-\alpha_{gas}c_{gas}(L_1 - L_2))$$

Thus, we see that all the variations in the light source and the filter cancel. If the ratio $$\frac{D_1}{D_2}$$

of the responsivities of the detectors is known or calibrated at a known concentration of gas, then one can use this to determine directly any concentration of the gas.

This cancellation of light source characteristics makes the entire detection system independent of the intensity as well as spectral variations in the light source over time, temperature, mechanical stresses and many other parameters that might change the characteristics of LS and filter over time.

Calibration step may be written as:

$$R_0 = \frac{D_1}{D_2}\exp(-\alpha_{gas}c_0\Delta L)$$

And the ratio noted and saved as part of the instrument calibration.

Now the measurement at any gas concentration may be determined as:

$$\frac{R}{R_0} = \exp(-\alpha_{gas}(c_{gas} - c_0)\Delta L)$$

Or,

-continued $$c_{gas} = c_0 + \frac{1}{\alpha_{gas}\Delta L}\log\left(\frac{R}{R_0}\right)$$

There are many implementations that will achieve the differential path of $\Delta L$. Some of these are drawn in FIG. 2.

Figure 2:
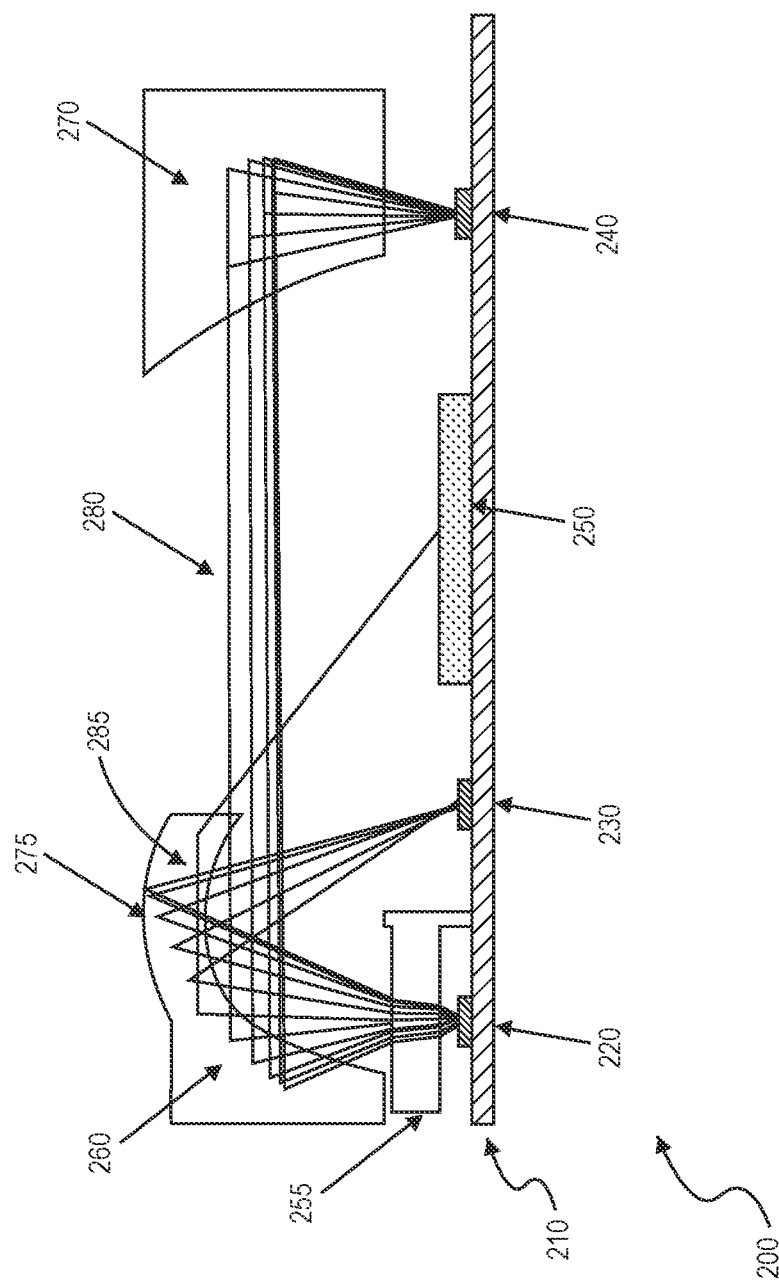
FIG. 2 depicts an exemplary differential path length measurement system for measuring gas concentration using beam splitting mirrors, in accordance with others embodiments of the disclosure provided herein.

FIG. 2 depicts an exemplary differential path length measurement system for measuring gas concentration using beam splitting mirrors, in accordance with others embodiments of the disclosure provided herein.

Differential path length (DPL) automatically cancels the changes in LED and filter's performance characteristics such as changes in intensity or wavelength and makes for a robust measurement of gas absorption. For example, the product of LED intensity in a wavelength range of gas absorption and photodiode responsivity can change by almost 10×-30× over temperature range of −40 to 70° C. The DPL method eliminates most of this variation and the ratio becomes stable to a few percent over the same temperature range. But there remains residual variation from mechanical changes in the optical path.

Ideally, we would like to make the ratio stable to 0.1% or better over temperature and other environmental conditions. The residual uncompensated changes in the DPL method seem to originate in the changes in the optical path itself. In this disclosure, we build on DPL method and compensate for the optical path changes as well as any other residual changes in the detector and amplifier to make the measurement of the absorption of gas robust.

Changes in the optical path lead to changes in the measured intensity that can't be distinguished from changes due to gas absorption (even after using DPL method). These include: Vibration; Temperature induced changes in size and distortion of the optical surfaces; Humidity induced changes in size and distortion of the optical surfaces; Changes in the reflectance of the surfaces; and Changes in the responsivity of the photodiodes as a function of temperature and environment.

All the above variations can be automatically compensated by implementing a new method of a ratio of ratio (RoR). RoR is described below in greater detail.

Three methods to substantially follow the same optical path by using off-resonance LED ($2^{nd}$ LED) at a different wavelength: $2^{nd}$ LED is reflected off the surface of the first LED; Additional package design—special filter design; Using stacked LEDs two provide two colors; Placing $2^{nd}$ LED very close to the first thereby guaranteeing similar paths by using optics that map the two slightly separated LED sources to the same reference and the main photodiodes.

An exemplary design has been realized in practice as shown in the FIG. 2. FIG. 2 is a side view of the module implementing differential path length measurement. FIG. 2 depicts an exemplary differential path length measurement system for measuring gas concentration using beam splitting mirrors, in accordance with others embodiments of the disclosure provided herein.

Differential path length module 200 comprises substrate 210, LED 220, reference detector 230, main detector 240, ASIC 250, optical filter 255, mirror 260, mirror 285, mirror 270, and beamsplitter 275. The optical filter 255 is placed directly above light source 220 and is made on silicon substrate 210. A complex reflector shape collimates part of the filtered light towards the main detector 240 and another portion is focused towards the reference detector 230. In one or more embodiments, the complex reflector shape functions as a beamsplitter 275, which will now be discussed in greater detail.

Beamsplitter 275 comprises mirror 260 and mirror 285. Mirror 260 is an off-axis parabola and mirror 285 is elliptical mirror. Two- and three-dimensional parabolas/paraboloids and ellipses/ellipsoids are preferred in some embodiments. Yet other conic sections and other shapes and surfaces are not beyond the scope of the present disclosure. For example, a polarizing beamsplitter (PBS) with plane mirrors could be used. Mirror 270 collects the collimated light having passed thru the gas and focuses it on the main detector 240. In some embodiments mirror 270 is a conic section, while in others it is a concave collimating lens. Any suitable reflecting shape or material is not beyond the scope of the present disclosure.

In practice and in some embodiments, light source 220 produces broad band light which is filtered by filter 255. The optical filter 255 can be bandpass filter chosen for the type of target gas of absorption. That is, the color of the light is selected based on the gas to be detected. In other embodiments, a rotating color wheel can be implemented, similar to an optical chopper. An optical chopper is a device which periodically interrupts a light beam. This gives rise to detecting numerous gasses at once.

Filtered light gets split into two paths: a collimated portion which is reflected off of mirror 260, traverses the gas absorption region 280 of the chamber and received by main detector 240; and portion that get reflected to reference detector 230. ASIC is then used to process the detector signals while processing any necessary ratios, in one or more embodiments. An application-specific integrated circuit is an integrated circuit (IC) chip customized for a particular use, rather than intended for general-purpose use.

Other circuits are not beyond the scope of the current disclosure, such as, FPGAs, ADCs and AFEs. A field-programmable gate array (FPGA) is an integrated circuit designed to be configured by a customer or a designer after manufacturing—hence the term "field-programmable." A field-programmable gate array (FPGA) is an integrated circuit designed to be configured by a customer or a designer after manufacturing—hence the term "field-programmable." An analog-to-digital converter (ADC, A/D, or A-to-D) is a system that converts an analog signal, such as a sound picked up by a microphone or light entering a digital camera, into a digital signal. An analog front-end (AFE or analog front-end controller AFEC) is a set of analog signal conditioning circuitry that uses sensitive analog amplifiers, often operational amplifiers, filters, and sometimes application-specific integrated circuits for sensors, radio receivers, and other circuits to provide a configurable and flexible electronics functional block needed to interface a variety of sensors to an antenna, analog-to-digital converter or, in some cases, to a microcontroller.

As was described, there is cancellation of intensity and wavelength shift of the LED over temperature and other environmental parameters. Note that common-mode shifts in temperature performance of the photodetector and the amplifier denoted by D is also compensated.

This is shown in the equation below (reproduced from DPL):

$$R_1 = \frac{S_{1Main}}{S_{1Ref}} = \frac{L_1 F_1 \eta_{Main} D_{1Main} \exp(-\alpha_{gas} c_{gas} L_1)}{L_1 F_1 \eta_{Ref} D_{1Ref} \exp(-\alpha_{gas} c_{gas} L_2)} = \quad (1)$$

$$\frac{\eta_{Main} D_{1Main}}{\eta_{Ref} D_{1Ref}} \exp(-\alpha_{gas} c_{gas}(L_1 - L_2))$$

Note that η represents optical splitting efficiency of the LED light as portion of the light is sent to the main detector and another portion sent to the reference detector. As one can see from the equation, the optical splitting is not cancelled and any changes in the ratio $\eta_{Main}/\eta_{Ref}$ can't be distinguished from the exponential term representing absorption by the gas. For example, if the beam splitter shifts relative to the LED/PDs due to any reason (e.g. from stress or expansion/contraction due to temperature), it may increase the light going to main PD and decrease it to reference PD thus changing the ratio $\eta_{Main}/\eta_{Ref}$. The idea is to compensate this too.

Now imagine we arranged a second source of light that substantially follows the same optical path but is not absorbed by the gas. Now we make two measurements. First using the first LED that measures the gas absorption and then immediately measure using the second LED that is known to be not absorbed by any other gas that might be present. Ratio at the second LED wavelength will look just like equation (1) except for the missing absorption term. This is written as:

$$R_2 = \frac{S_{2Main}}{S_{2Ref}} = \frac{L_2 F_2 \eta_{Main} D_{2Main}}{L_2 F_{21} \eta_{Ref} D_{2Ref}} = \frac{\eta_{Main} D_{2Main}}{\eta_{Ref} D_{2Ref}} \quad (2)$$

Now we can form the ratio of ratio (RoR) and it can be readily seen that η's will cancel too. Thus, RoR will eliminate any drift caused by mechanical shift of the optical components either from stress or temperature. RoR is:

$$RoR = \frac{R_1}{R_2} = \frac{\frac{\eta_{Main} D_{1Main}}{\eta_{Ref} D_{1Ref}} \exp(-\alpha_{gas} c_{gas}(L_1 - L_2))}{\frac{\eta_{Main} D_{2Main}}{\eta_{Ref} D_{2Ref}}} = \quad (3)$$

$$\frac{\left(\frac{D_{1Main}}{D_{2Main}}\right)}{\left(\frac{D_{1Ref}}{D_{2Ref}}\right)} \exp(-\alpha_{gas} c_{gas}(L_1 - L_2))$$

Consider the first term:

$$\left(\frac{D_{1Main}}{D_{2Main}}\right).$$

This ratio is measured on a physically the same detector connected to the same electronics. Any changes in the detector characteristics that are common to both the wavelengths such as amplifier gain, detector's shunt impedances etc. will all cancel as a function of temperature or some other environmental parameter. A potentially small and residual wavelength dependent change in these parameters may remain uncompensated. But the second term $$\left(\frac{D_{1Ref}}{D_{2Ref}}\right)$$

has the same characteristics—as it is made from the same material and made together in manufacturing process and will divide the first term in equation (3) and thus the pre-factor, $$\gamma \equiv \frac{\left(\frac{D_{1Main}}{D_{2Main}}\right)}{\left(\frac{D_{1Ref}}{D_{2Ref}}\right)} \qquad (4)$$

is to the maximum extent possible independent of the environmental factors. Now we can proceed to calibrate the device for gas concentration much as we discussed in DPL.

In the absence of any gas, we write equation (4) as:

$$\text{RoR}(c_{gas}=0)=\gamma \qquad (5)$$

This ratio can be saved in memory and then the gas concentration is measured by:

$$\frac{\text{RoR}(c_{gas})}{\text{RoR}(c_{gas}=0)} = \exp(-\alpha_{gas}c_{gas}(L_1-L_2)) \approx 1 - \alpha_{gas}c_{gas}(\Delta L) \qquad (6)$$

The approximate right-hand term in Equation (6) applies when the argument of exponential is small.

With this method, we have achieved direct calibration free measurement of gas concentration. It only requires the knowledge of optical path length and average gas absorption $\alpha_{gas}$. Note that for many popular gases such as $CO_2$ or $CH_4$ etc. absorption cross-section can be calculated for a given LED and optical filter.

In general, $2^{nd}$ LED and the $1^{st}$ LED after passing thru the filter can both have common absorption regions. In which case, the common absorption region will still be cancelled.

Methods of Achieving RoR

Method 1: Second LED is Reflected Off the Surface of the First LED

Figure 3:
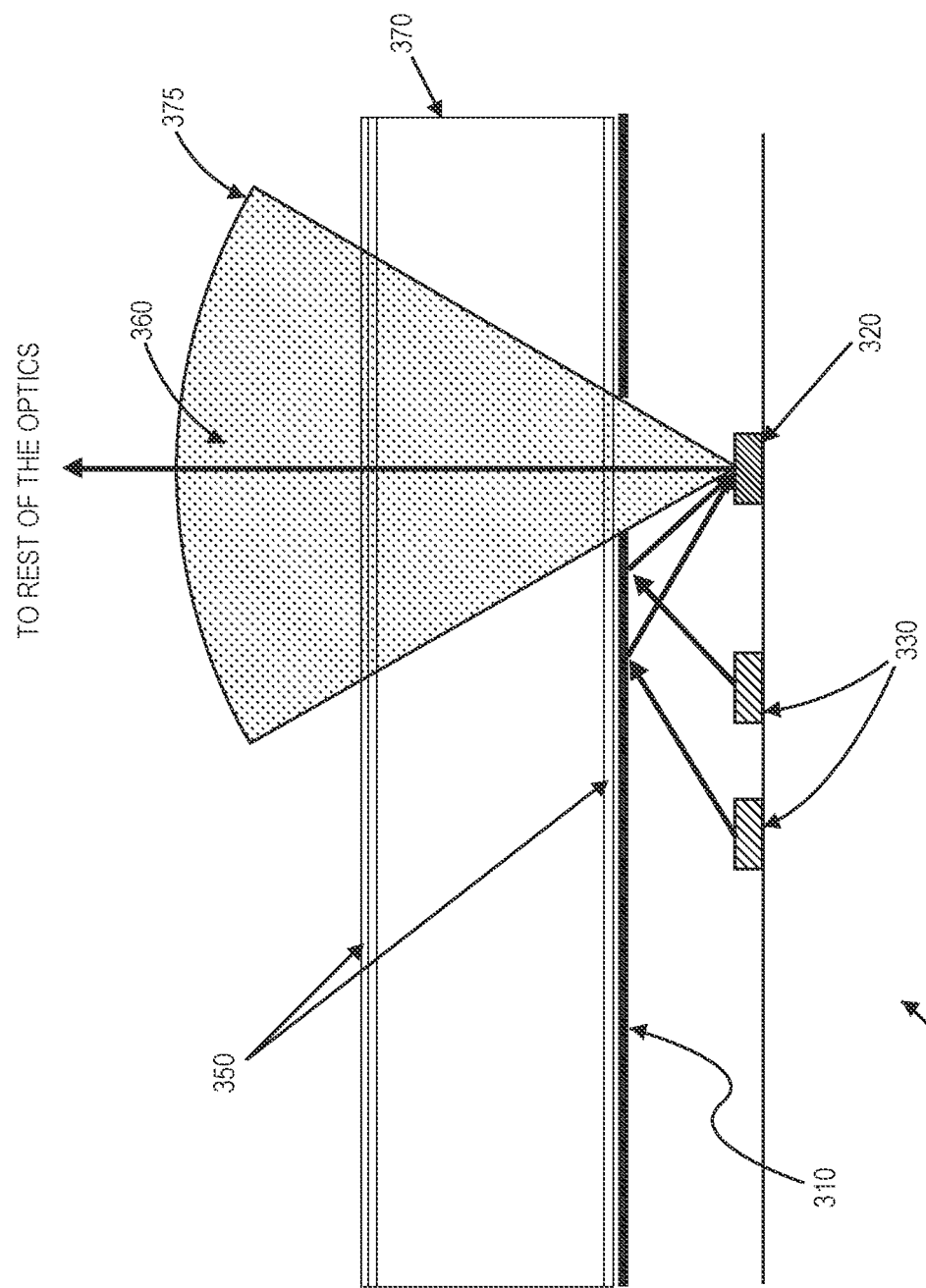
FIG. 3 depicts an exemplary differential path length measurement system using alternate beam path optics, in accordance with others embodiments of the disclosure provided herein.

In this method we take advantage of the fact that we have a filter surface (as shown in FIG. 3). We add another LED in the near infra-red that can be transmitted by the filter F and place it close to the primary or the first LED. By patterning the filter as shown in the figure below, we can force the rays from the $2^{nd}$ LED to follow the path of the first LED.

FIG. 3 depicts an exemplary differential path length measurement system 300 using alternate beam path optics, in accordance with others embodiments of the disclosure provided herein. Differential path length measurement system 300 comprises a primary/first LED 320, secondary LED 330, mirror 310, filters 350, and substrate 370.

FIG. 3 is a cross-section of the region near the first LED 320 used for measuring gas absorption. Second LED 330 is placed in close proximity to the first LED. FIG. 3 shows an exemplary range for secondary 330 placement. Light from secondary LED 330 is reflected off of mirror 310. Mirror 330 can be made from silvering, dielectric coating, or any other suitable manner which is well known in the art. In the present embodiment, mirror 330 reflects light at or near the bandwidth of LED 330. At minimum, their bandwidths should overlap such that light from LED 330 is substantially reflected.

The coating of glass with a reflective layer of a metal is generally called "silvering," even though the metal may not be silver. Currently the main processes are electroplating, "wet" chemical deposition, and vacuum deposition. Front-coated metal mirrors achieve reflectivities of 90-95% when new.

Dielectric coating applications achieve higher reflectivity or greater durability, where wide bandwidth is not essential. Dielectric coatings can achieve reflectivities as high as 99.997% over a limited range of wavelengths. Because they are often chemically stable and do not conduct electricity, dielectric coatings are almost always applied by methods of vacuum deposition, and most commonly by evaporation deposition. Because the coatings are usually transparent, absorption losses are negligible. Unlike with metals, the reflectivity of the individual dielectric-coatings is a function of Snell's law known as the Fresnel equations, determined by the difference in refractive index between layers. Therefore, the thickness and index of the coatings can be adjusted to be centered on any wavelength. Vacuum deposition can be achieved in a number of ways, including sputtering, evaporation deposition, arc deposition, reactive-gas deposition, and ion plating, among many others.

Mirror 310 is modified and patterned to have opening over the top of first LED while the rest of the surface is metallized or acts as high reflectivity mirror 310 at the second LED 330 wavelength.

When the second LED 330 is turned on, the light is reflected from the mirror-like surface and some of it strikes the first LED 320 which can be very close by. This is limited by the distance between the first and second LED and the cone of emission. Meaning, the light from second LED 330 won't properly impinge the first LED 320 if the distance between them are too great or if the light cone is too narrow.

Invariably, the rough surface of the first LED 320 or other structures near-by such as bond pad or bond wires will scatter light in the same direction as the light from the first LED 320. This scattered light is the only light that will reach the rest of the optics and follow the same path as the first LED 320. Thus, we have achieved our goal of making the two LEDs have substantially the same path. Note that the intensity of the light from the second LED does not matter as shown in other embodiments, particularly those incorporated by reference. Nevertheless, it should be enough to produce a high-quality measurement to form an RoR calculation.

In one of the embodiments, the substrate on which the filter is formed is silicon and hence the second LED must be in wavelength region that is substantially transparent to silicon. Filters 350 can be made pursuant to the preceding discussion in the present disclosure. The center wavelength of filters 350 are chosen for particular applications. For example, they could be bandpass for a particular gas to be detected.

In practice, light from secondary LED 330 is reflected off of mirror 310. This light is then incident on primary LED 320. Primary LED light has cone of emission 375, as demonstrated in FIG. 3. The primary optical measurement pathway 360 continues to rest of the system optics. One of ordinary skill in the art can appreciate that some of light from secondary LED will travel collinearly with pathway 360 after scattering and/or reflection of primary LED 320.

Method 2: Using Stacked LEDs

In this case a bigger LED is placed at the bottom and the other LED placed on top. Since both the LED's are within the focal region of the lens and effectively are very close to each other, the light from each LED follows the same path. This is shown in the FIG. 4.

Figure 4:
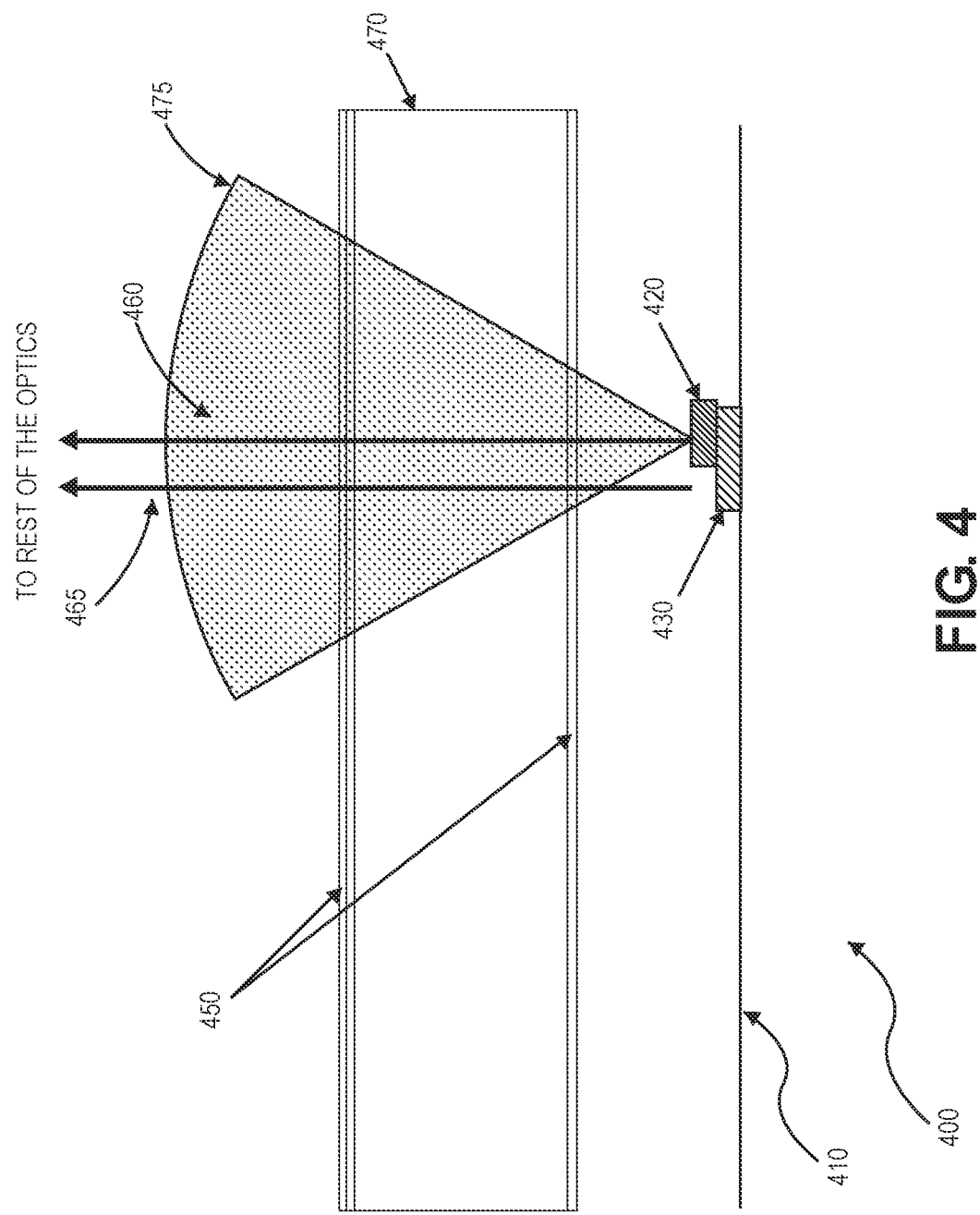
FIG. 4 illustrates an exemplary differential path length measurement system using alternate beam path optics, in accordance with others embodiments of the disclosure provided herein.

FIG. 4 illustrates an exemplary differential path length measurement system using alternate beam path optics, in accordance with others embodiments of the disclosure provided herein. FIG. 4 depicts an exemplary differential path length measurement system 400 using alternate beam path optics, in accordance with others embodiments of the disclosure provided herein. Differential path length measurement system 400 comprises a primary/first LED 420, secondary LED 430, filters 450, printed circuit board (PCB) 410 and substrate 470.

FIG. 4 is a cross-section of the region near the first LED 420 used for measuring gas absorption. Second LED 430 is placed in close proximity to the first LED. In one or more embodiments, first LED 420 is disposing on top of second LED 430. Light from secondary LED 330 produces a near collinear light propagation 465 as that of the primary optical measurement path 460.

Thus, we have achieved our goal of making the two LEDs have substantially the same path. Note that the intensity of the light from the second LED does not matter as shown in other embodiments, particularly those incorporated by reference. Nevertheless, it should be enough to produce a high-quality measurement to form an RoR calculation.

In one of the embodiments, the substrate on which the filter is formed is silicon and hence the second LED must be in wavelength region that is substantially transparent to silicon. Filters 450 can be made pursuant to the preceding discussion in the present disclosure. The center wavelength of filters 450 are chosen for particular applications. For example, they could be bandpass for a particular gas to be detected.

In practice, light from secondary LED 430 and primary LED 420 produce a substantially similar cone of emission 475, as demonstrated in FIG. 4. The primary optical measurement pathways 460, 465 continues to rest of the system optics. One of ordinary skill in the art can appreciate that some of light from secondary LED will travel collinearly with the primary optical measurement pathway. 460.

In this case we take advantage of the fact that the collection optics are designed to collect light from a LED surface that may have extent of couple hundred microns. The light from the entire surface of the LED needs to be collected and imaged onto the detector surface. Thus, two LEDs placed on top one another will be indistinguishable and still form an image on the detector surface. The choice of which wavelength should have a larger LED will be determined by the cost and electrical convenience.

Clearly, this method can be extended and becomes almost perfect if an LED is constructed to emit at two different wavelengths and electrically selected to emit at any one of the wavelengths.

While the discussion has used a specific optical module by way of example to describe the invention, but it is not limited to any particular optical arrangement of beamsplitters and collimation optics. It is to be understood that the measurement of RoR is independent of how differential path length is specifically arranged. There are many cases in which one needs to measure extremely low concentration of a gas.

In this case, the optical path length must be long to provide sufficient absorption. But longer differential path length is even more likely to suffer from mechanical changes in the optical collection efficiency as environment changes by way of temperature or stress or humidity etc. And at the same time, one needs to measure even smaller changes as gas concentration is low. The method disclosed here becomes even more powerful for ultra-sensitive absorption measurement as it fully compensates for the mechanical as well as changes in the LED, PD, amplifiers etc. leaving only the absorption of gas as measured parameter. When perfected, the solution show in this invention can be used to directly calibrate the gas concentration based directly on the first principle measurement.

Historically, in most cases, the inherent stability over environment is never achieved by the physical device but rather this is done by long and arduous calibration. A look-up table is built to compensate the expected changes by measuring environmental parameters like temperature and humidity. For ultra-precise measurement, the entire device is temperature stabilized. We are able to achieve this without either of these costly and laborious measures.

SELECT EXAMPLES

Example 1 provides an apparatus for optical differential path length gas detection comprising a first light source producing a first light centered at a first wavelength, a second light source producing a second light centered at a second wavelength, a light filter disposed proximally to the first light source and configured to pass the second light, and a mirror configured to reflect the second light onto the beamsplitter first light source.

Example 2 provides for the optical differential path length gas detector according to any of the preceding and/or proceeding examples further comprising a circuit configured to calculate a ratio of signals which represent measured intensities of the first and second light.

Example 3 provides for the optical differential path length gas detector according to any of the preceding and/or proceeding examples, wherein the circuit is an ASIC.

Example 4 provides for the optical differential path length gas detector according to any of the preceding and/or proceeding examples, wherein the circuit is an AFE.

Example 5 provides for the optical differential path length gas detector according to any of the preceding and/or proceeding examples further comprising a controller configured to control the current to the first and second light source.

Example 6 provides for the optical differential path length gas detector according to any of the preceding and/or proceeding examples further comprising a first photodetector configured to detect light centered at the first wavelength, the first photodetector producing a first signal indicative of measured intensity.

Example 7 provides for the optical differential path length gas detector according to any of the preceding and/or proceeding examples further comprising a first photodetector configured to detect light centered at the second wavelength, the second photodetector producing a second signal indicative of measured intensity.

Example 8 provides for the optical differential path length gas detector according to any of the preceding and/or proceeding examples further comprising a circuit configured to calculate a first ratio based at least on the first and second signals.

Example 9 provides for the optical differential path length gas detector according to any of the preceding and/or proceeding examples, wherein the circuit is further configured to calculate a ratio of ratios based at least on the first ratio.

Example 10 provides for the optical differential path length gas detector according to any of the preceding and/or proceeding examples further comprising a second filter configured to pass the first light.

Example 11 provides for the optical differential path length gas detector according to any of the preceding and/or proceeding examples further comprising a time multiplexer, wherein the time multiplexer is configured alternate between first and second signals.

Example 12 provides for an apparatus for optical differential path length gas detection comprising a first light source producing a first light cone centered at a first wavelength, a second light source producing a second light cone centered at a second wavelength, and a light filter disposed proximally to the first light source and configured to pass the second light, wherein, the first and second light cones substantially overlap.

Example 13 provides for the optical differential path length gas detector according to any of the preceding and/or proceeding examples, wherein the first light source is disposed directly adjacent to the second light source.

Example 14 provides for the optical differential path length gas detector according to any of the preceding and/or proceeding examples, wherein the first light source is disposed directly on top of the second light source.

Example 15 provides for the optical differential path length gas detector according to any of the preceding and/or proceeding examples further comprising a circuit configured to calculate a first ratio of signals which represent measured intensities of the first and second light.

Example 16 provides for the optical differential path length gas detector according to any of the preceding and/or proceeding examples, wherein the circuit is further configured to calculate a ratio of ratios based at least on the first ratio.

Example 17 provides for the optical differential path length gas detector according to any of the preceding and/or proceeding examples, wherein the first and second light sources are LEDs.

Example 18 provides for the optical differential path length gas detector according to any of the preceding and/or proceeding examples further comprising a controller configured to control the current to the first and second light source.

Example 19 provides for the optical differential path length gas detector according to any of the preceding and/or proceeding examples further comprising a second filter configured to pass the second light.

Example 20 provides for a method for calculating optical differential path length gas detection comprising emitting a first light from a first LED, the first light centered at a first wavelength; emitting a second light from a second LED, the second light centered at a second wavelength, reflecting the second light off the first LED, measuring the first light, measuring the second light; and calculating a ratio of ratios based at least on the measurement of the first and second light.

The above description of illustrated embodiments, including what is described in the Abstract, is not intended to be exhaustive or limiting as to the precise forms disclosed. While specific implementations of, and examples for, various embodiments or concepts are described herein for illustrative purposes, various equivalent modifications may be possible, as those skilled in the relevant art will recognize. These modifications may be made in light of the above detailed description, the Abstract, the Figures, or the claims.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

INTERPRETATION OF TERMS

All definitions, as defined and used herein, should be understood to control over dictionary definitions, definitions in documents incorporated by reference, and/or ordinary meanings of the defined terms. Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. An optical differential path length gas detector comprising:
    a first light source producing a first light centered at a first wavelength;
    a second light source producing a second light centered at a second wavelength;
    an optical filter disposed proximally to the first light source and configured to selectively pass the second light; and
    a mirror configured to reflect the second light onto the first light source, wherein a portion of the reflected second light travels collinearly with the first light,
    wherein the first light source has a surface from which the first light is emitted, wherein the second light source has a surface on which the second light is reflected, and wherein a main surface of the optical filter and a main surface of the mirror are substantially parallel to the surface of the first light source and the surface of the second light source.

2. The optical differential path length gas detector of claim 1, further comprising a circuit configured to calculate a ratio of signals which represent measured intensities of the first and second light.

3. The optical differential path length gas detector of claim 2, wherein the circuit is an application-specific integrated circuit (ASIC).

4. The optical differential path length gas detector of claim 2, wherein the circuit is an analog front end (AFE).

5. The optical differential path length gas detector of claim 1, further comprising a controller configured to control a current to the first and second light source.

6. The optical differential path length gas detector of claim 1, further comprising a first photodetector configured to detect light centered at the first wavelength, the first photodetector producing a first signal indicative of a first measured intensity.

7. The optical differential path length gas detector of claim 6, further comprising a second photodetector configured to detect light centered at the second wavelength, the second photodetector producing a second signal indicative of a second measured intensity.

8. The optical differential path length gas detector of claim 7, further comprising a circuit configured to calculate a first ratio based at least on the first signal and the second signal.

9. The optical differential path length gas detector of claim 8, wherein the circuit is further configured to calculate a ratio of ratios based at least on the first ratio.

10. The optical differential path length gas detector of claim 1 further comprising a second optical filter configured to pass the first light.

11. The optical differential path length gas detector of claim 7, further comprising a time multiplexer configured to alternate between the first signal and the second signal.

12. An optical differential path length gas detector comprising:
    a first light source producing a first light cone centered at a first wavelength;
    a second light source producing a second light cone centered at a second wavelength, wherein the first light source is disposed on top of the second light source; and
    an optical filter disposed proximally to the first light source and configured to selectively pass the second light;
    a mirror configured to reflect the second light cone onto the first light source, wherein a portion of the reflected second light cone travels collinearly with the first light cone,
    wherein, the first light cone and the second light cone substantially overlap,
    wherein the first light source has a surface from which the first light cone is emitted, wherein the second light source has a surface on which the second light cone is reflected, and wherein a main surface of the optical filter and a main surface of the mirror are substantially parallel to the surface of the first light source and the surface of the second light source.

13. The optical differential path length gas detector of claim 12, wherein the first light source is disposed directly adjacent to the second light source.

14. The optical differential path length gas detector of claim 12, wherein the first light source is disposed directly on top of the second light source.

15. The optical differential path length gas detector of claim 12, further comprising a circuit configured to calculate a first ratio of signals which represent respective measured intensities of the first light and the second light.

16. The optical differential path length gas detector of claim 15, wherein the circuit is further configured to calculate a ratio of ratios based at least on the first ratio.

17. The optical differential path length gas detector of claim 12, wherein the first light source is a first light emitting diode (LED) and the second light source is a second LED.

18. The optical differential path length gas detector of claim 12, further comprising a controller configured to control a current to the first light source and the second light source.

19. The optical differential path length gas detector of claim 12, further comprising a second optical filter configured to selectively pass the second light.

20. A method for calculating optical differential path length gas detection comprising:
- emitting a first light from a first light emitting (LED), the first light centered at a first wavelength;
- emitting a second light from a second LED, the second light centered at a second wavelength;
- selectively passing the second light using an optical filter;
- reflecting the second light onto a surface of the first LED using a mirror;
- measuring the first light;
- measuring the second light; and
- calculating a ratio of ratios based at least on a measurement of the first light and a measurement of the second light,
- wherein the first LED has a surface from which the first light cone is emitted, wherein the second LED has a surface on which the second light cone is reflected, and wherein a main surface of the optical filter and a main surface of the mirror are substantially parallel to the surface of the first LED and the surface of the second LED.

* * * * *